United States Patent [19]
Freitag

[11] Patent Number: 5,803,080
[45] Date of Patent: Sep. 8, 1998

[54] INSTRUMENT FOR INTERVENTIONAL FLEXIBLE TRACHEOSCOPY/ BRONCHOSCOPY

[75] Inventor: Lutz Freitag, Hemer, Germany

[73] Assignee: Willy Rüsch AG, Kernen, Germany

[21] Appl. No.: 771,297

[22] Filed: Dec. 20, 1996

[30] Foreign Application Priority Data

Dec. 20, 1995 [DE] Germany .......................... 195 47 538.0

[51] Int. Cl.⁶ .................................................. A61M 16/00
[52] U.S. Cl. ............................... 128/207.14; 128/200.26; 128/207.15; 128/207.18
[58] Field of Search ........................ 128/207.14, 207.15, 128/207.18, 200.26, 6, 912; 604/280

[56] References Cited

U.S. PATENT DOCUMENTS

| | | | |
|---|---|---|---|
| 4,444,185 | 4/1984 | Shugar | 128/200.26 |
| 4,446,864 | 5/1984 | Watson et al. | 128/207.14 |
| 4,567,882 | 2/1986 | Heller | 128/200.26 |
| 4,685,457 | 8/1987 | Donenfeld | 128/207.14 |
| 4,819,664 | 4/1989 | Mazari | 128/207.15 |
| 5,131,380 | 7/1992 | Heller et al. | 128/6 |
| 5,285,778 | 2/1994 | Mackin | 128/200.26 |
| 5,400,771 | 3/1995 | Pirak et al. | 128/200.26 |
| 5,499,625 | 3/1996 | Frases et al. | 128/200.26 |
| 5,660,175 | 8/1997 | Dayal | 128/200.26 |

FOREIGN PATENT DOCUMENTS

| | | | |
|---|---|---|---|
| 4115497 | 11/1992 | Germany | A61M 16/04 |
| 1528279 | 10/1978 | United Kingdom | 128/200.26 |
| 9117789 | 11/1991 | WIPO | A61M 29/02 |

*Primary Examiner*—Mickey Yu
*Assistant Examiner*—V. Srivatava
*Attorney, Agent, or Firm*—Friedrich Kueffner

[57] ABSTRACT

An instrument for interventional flexible tracheoscopy/ bronchoscopy, particularly for the treatment of central air passage stenoses under local anesthesia with the aid of a flexible fiber bronchoscope, includes an outer tube and an inner tube, wherein the outer tube and the inner tube can be displaced relative to each other, and wherein at least one guide element is provided for positioning the inner tube relative to the outer tube and a cuff which can be filled with a medium is arranged in the area of the distal end of the inner tube.

8 Claims, 3 Drawing Sheets

INSTRUMENT FOR INTERVENTIONAL FLEXIBLE TRACHEOSCOPY/ BRONCHOSCOPY

BACKGROUND OF THE INVENTION

1. Field of the Invention

The present invention relates to an instrument for interventional flexible tracheoscopy/bronchoscopy, particularly for the treatment of central air passage stenoses under local anesthesia with the aid of a flexible fiber bronchoscope.

2. Description of the Related Art

In bronchoscopy or tracheoscopy, the direct observation of the bronchial tree or the trachea is carried out by means of a bronchoscope. In addition to diagnostic observation, bronchoscopy or tracheoscopy also serve for the removal of tissue samples, for the removal of foreign bodies and for carrying out other therapeutic treatments, such as laser therapy or radiation therapy or the placement of prostheses.

There are essentially two methods for carrying out the bronchoscopy or tracheoscopy.

In the first method, a rigid tube, usually equipped with an independent light source, observation magnifier, angular lens system or other lens system, is inserted through the mouth into the trachea. The instruments required for treatment are then introduced through the rigid bronchoscope and are actuated. Respiration of the patient takes place through the tube.

In accordance with the other method, initially a flexible tracheal tube is placed and a flexible fiber bronchoscope is guided through the tube. It is also possible to insert the fiber bronchoscope alone or next to the flexible tube. In this case, respiration of the patient is spontaneous.

The insertion of a respiration tube from the mouth or nose into the larynx or trachea is known from endotracheal intubation. The outer end of the tube is provided with an expandable cuff to provide a complete sealing action. After the tube has been inserted into the trachea and has been placed into the correct position, the cuff is expanded, so that the surface of the cuff rests against the mucous membrane of the trachea and closes off the outer area in an air-tight manner. Such an endotracheal tube is known, for example, from DE-OS 41 15 497. The fiber bronchoscope is then inserted through the tube.

In accordance with another possibility, double lumens are used which are composed of two tubes which are joined to each other, wherein one of the tubes is intended for the respiration of the patient.

Laser operations in the areas of the pharynx and larynx with the aid of endotracheal tubes and bronchoscope have also been carried out successfully in recent years.

So-called stents are used in the treatment of stenoses of the larynx. A stenosis is a congenital or acquired narrowing of a body tube. A stents hold the body tube open as an internal support member and, thus, acts as a spacer member. An appropriate tool is required for the insertion of the stent. Such a tool is known, for example, from WO 91/17789. In that case, the stent is held together in a flexible tube during the insertion process. For placing the stent, the stent is released by means of a pusher. Depending on the type of configuration of the stent, the stent expands into its expanded position either by itself as a result of its natural tension or with the aid of a dilator.

A general problem in the diagnosis and therapy of pulmonary defects, bronchial defects or tracheal defects is the fact that the instruments must be inserted from the mouth or the nose into the larynx or the trachea, wherein it is necessary to pass the area of the vocal cords in the larynx. However, with a diameter of about 15 mm, the maximum open width of the larynx in the area of the vocal cords is very narrow, so that the inserted instruments take away a very large portion of the free lumen. Consequently, the spontaneous respiration of the patient is impaired. In addition, there is the danger that the vocal cords are injured.

In the case of laser treatment, irritations of the mucous membrane as a result of laser smoke may occur. In the other hand, in the case of radiation treatment (brachytherapy), ulcerous changes can be observed at those locations where the tube carrying the radiation medium rests due to its spring stiffness against the inner wall of the trachea.

Moreover, it appears that the known instruments for inserting and placing stents can be improved. Especially in the case of stents whose activation requires a heat application to the stent, it is useful to provide a suitable tool.

SUMMARY OF THE INVENTION

Therefore, it is the primary object of the present invention to provide an instrument for tracheoscopy/bronchoscopy which can be inserted gently into the larynx or the trachea, which ensures a good utilization of the available space and which makes it possible to carry out active therapeutic measures, wherein the instrument is to be particularly suitable for the introduction and placement of stents.

In accordance with the present invention, an instrument for interventional flexible tracheoscopy/bronchoscopy includes an outer tube and an inner tube, wherein the outer tube and the inner tube can be displaced relative to each other, and wherein at least one guide element is provided for positioning the inner tube relative to the outer tube and a cuff which can be filled with a medium is arranged in the area of the distal end of the inner tube.

The inner tube is composed of a thin elastic synthetic material, such as polyurethane or Teflon. The inner tube is guided over a conventional fiber bronchoscope. At its proximal end, the inner tube has a standard adaptor or connector. At its distal end, the inner tube is equipped with a cuff which can be filled with a medium. A thin additional duct through which the cuff can be filled and emptied is provided in the wall of the inner tube. However, the supply line for the cuff can also be guided on the inside or the outside of the wall of the inner tube. Gases or liquids can be used for expanding the cuff.

The outer tube is preferably manufactured of stiffer synthetic material. Since the open width of the larynx in the area of the vocal cords is very limited, the outer diameter of the outer tube should not be substantially greater than 11 mm. The length of the outer tube is shorter than that of the inner tube.

An annular gap having a width of about 2.5 mm exists between the inner tube and outer tube. The free space available as a result is sufficient for ensuring a safe respiration, even if the bronchoscope is inserted into the inner tube.

The inner tube and the outer tube can be displaced relative to each other in longitudinal direction as well as in axial direction. Guide elements ensure a problem-free sliding movement and prevent the undesirable contact between the tubes and they prevent closing of the annular gap required for respiration.

On the other hand, the axial position of the inner tube in the outer tube can be determined by the appropriate arrangement and position of the guide elements. Also, the inner tube can be rotated about the longitudinal axis in the outer tube. This is particularly an advantage in brachytherapy, since the position of the hose portion with the radiation medium can be placed precisely relative to the area to be treated and the surrounding tissue is essentially unaffected. It is also advantageous in this connection to construct a guide element in such a way that a circumference can be increased, for example, by blowing up. This increase of the circumference makes it possible to position the inner tube.

Even though it is basically possible to arrange the guide elements at the inner circumference of the outer tube, for example, in the form of lips or longitudinal ribs, a preferred embodiment of the invention provides that the guide elements are arranged at the inner tube. The guide elements can be released in the form of spacer members distributed over the length of the inner tube. A particularly practical embodiment of the guide elements is the configuration of the guide elements in the form of strands. These strands advantageously are thin lines which carry out additional supply purposes, such as the supply of oxygen or medicaments. The fillable cuff can also be actuated through one or more of the lines.

In accordance with the invention, it is also possible to arrange the guide elements on the inner circumference of the outer tube and the outer circumference of the inner tube in such a way that the rotary movement of the inner tube in the outer tube is limited. This can be effected, for example, by arranging a hose-like guide element on the inner circumference of the outer tube and by providing two guide elements for the inner tube. The guide element on the outer tube then forms a stop for the two other guide elements. In this manner, the inner tube is prevented from being twisted in the outer tube with the connected supply lines.

In accordance with a further development of the present invention, the guide elements are components of a multiple-duct tube. This results in an embodiment with three tubes which can be displaced relative to each other, wherein the tube in the middle has several ducts. It is basically conceivable that the tube in the middle forms a tube construction formed of individual hose lines.

In order to ensure a therapeutically correct manipulation of the instrument during the insertion of stents, it is advantageous if the axial position of at least the guide element at the distal end can be determined. This makes it possible to place stents of different lengths without problems with the aid of the instrument according to the invention. Advantageous in this connection is an embodiment with three tubes integrated with each other, because in that case, the position of the tube in the middle can be exactly determined as an abutment for the stent to be placed.

In contrast to tubes known in the past, respiration of the patient takes place through the inner tube, while the outer tube dilates or expands the trachea. During the intubation the cuff may be easily filled, so that the cuff covers the front rim portions of the outer tube and a gentle intubation without the risk of damage to the vocal cords is ensured.

The cuff functions as a multi-purpose balloon. As soon as the instrument is placed in its desired position, the cuff can be expanded for the duration of the treatment, so that its surface rests against the mucous membranes of the trachea and, thus, closes the outer area in an air-tight manner. This provides the advantage that respiration of the patient can be carried out in a controlled manner through the inner tube, while body fluids such as mucus or gastric juice cannot reach the lungs because of the barrier provided by the cuff.

Intubation anesthesia is also possible. Consequently, the instrument according to the present invention can be used as a normal balloon instrument.

If a certain area of the trachea is to be expanded, the cuff can be used as a dilation balloon for expanding these areas. Moreover, it is possible to use the cuff for stopping bleeding in the tracheal area by applying a compression pressure against the bleeding area.

A separate oxygen supply line may be provided. During the treatment, for example, by means of laser, the brachytherapy, the photodynamic therapy or the introduction of a stent, the patient receives oxygen through the oxygen supply line.

The instrument according to the present invention can be used particularly advantageously for the placement of stents. Such stents are available in various embodiments of metal and/or synthetic material. They usually are composed of a fabric of metal wires which expand by themselves as a result of their natural tension. Moreover, there are stents which must be expanded into the expanded position at the place of use by means of a suitable device, for example, a balloon catheter. Stents of a so-called shape memory alloy are also known. These stents have a small radial diameter at a low temperature, while they expand radially when exceeding an upper threshold temperature, so that they can keep a stenosis open in this manner. Only when dropping below a lower threshold temperature, the stent returns into its small state. It is particularly advantageous to use stents of an alloy of nickel and titanium, the so-called nitinol.

The instrument according to the present invention can be used for the placement of various stents, whether they are self-expanding stents or stents which require an activation. For this purpose, the stent is placed in the free space between the outer tube and the inner tube. Positioning of the stent in the instrument can be carried out in the area between the cuff and the first guide element at the distal end of the inner tube. Another possibility is to position the stent partially over the cuff. In its insertion position, the stent can be held by the guide elements.

When the stent is inserted, there is sufficient space for the respiration through the annular space or for the respiration through the internal space. After the stenosis has been passed, the outer shorter tube is retracted, so that the stent is released. A self-expanding stent then by itself assumes the expanded position. Subsequent positioning is possible by means of the cuff. The embodiment with three tubes makes it possible to push the stent out by means of the tube in the middle.

In the case of stents which require heat activation, for example, warm water can be pumped into the cuff in order to achieve a complete expansion of the stent. This process can be reversed by conducting a cold medium into the cuff.

Consequently, the cuff is a multi-purpose balloon which can be used for a safe intubation, for the dilation, for the application of heat or low temperatures, and as a normal blocking cuff.

The instrument according to the present invention further provides the advantage that a safe respiration is ensured even during the bronchoscopy. In the past, this was only possible with a relatively high risk when using stiff bronchoscopes.

The instrument according to the present invention provides further advantages. In the case of brachytherapy, the iridium radiation source can be positioned in the middle of the trachea over the inner tube. Since a contact of the line carrying the radiation source with the trachea or with the wall of the outer tube is prevented by the guidance in the inner tube, damage due to radiation, such as a radiogenic ulcer, is prevented.

The laser treatment can also be carried out more safely because the air passages are protected and complications, such as bleedings, can be counteracted or immediately stopped. In the case of the laser operations in areas of the pharynx and the larynx, there is the additional advantage that the laser smoke produced by the removal of the tissue is not breathed in by the patient.

The instrument according to the present invention is also particularly suitable for use in photodynamic therapy. In photodynamic therapy, a monochromatically intensive light is applied by means of a dye laser onto diseased tissue, so that tumors disintegrate. A homogenous light distribution is of particular importance. This can be achieved by manufacturing the inner tube of a material which is transparent but not opaque. Various opalescent materials are available for this purpose. A homogenous distribution of the light can be achieved as a result. The safety of the photodynamic therapy is increased.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DETAILED DESCRIPTION OF THE PREFERRED EMBODIMENTS

Figure 1:
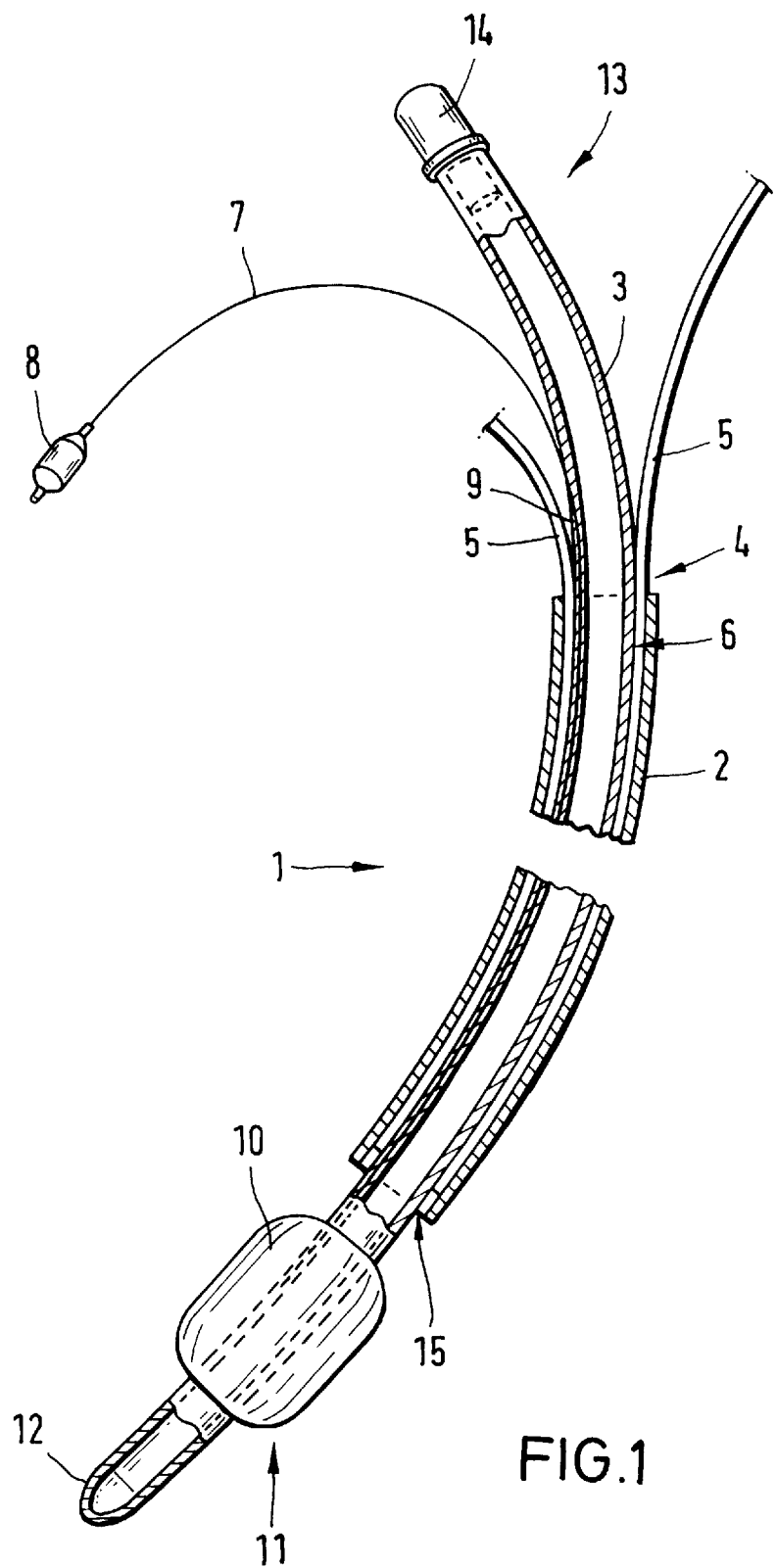
FIG. 1 is a schematic illustration of a first embodiment of an instrument for interventional flexible tracheoscopy/bronchoscopy according to the present invention.
Figure 4:
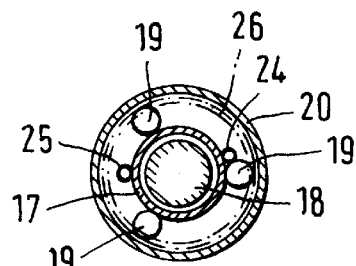
FIG. 4 is cross-sectional view of the instrument.

FIG. 1 of the drawing shows an instrument 1 for interventional flexible tracheoscopy/bronchoscopy. The instrument 1 includes essentially an outer tube 2 and an inner tube 3 which are displaceable relative to each other and spaced from each other by means of guide elements 4. The guide elements 4 are formed by supply lines 5. As shown in FIG. 4, three guide elements are arranged radially on the outer circumference 6 of the inner tube 3 and offset relative to each other by 120°.

FIG. 1 further shows a supply hose 7 with a control balloon 8. The supply hose 7 is guided in the wall 9 of the tube 3 and is in communication with a cuff 10 which can be filled with gas. The cuff 10 is arranged a short distance in front of the distal end 11 of the inner tube 3. FIG. 1 shows the cuff 10 in the expanded position. The distal end 11 further has a rounded end 12. The portion between the cuff 10 and the distal end 11 may be shorter than illustrated in FIG. 1.

The cuff can be utilized for aiding a safe intubation. It is particularly suitable for a dilation or for the application of warm water for expanding a temperature-sensitive stent. Of course, the cuff 10 can also be used as a normal blocking cuff.

A standard connector 14 is provided at the proximal end 13. A fiber bronchoscope, not shown, can be guided through the connector 14 into the inner tube 3. After insertion of the fiber bronchoscope, respiration of the patient takes place through the free space in the annular gap 15 between the inner tube 3 and the outer tube 2.

The inner tube 3 is of an opalescent, milky-colored, thin polyurethane. Its length is preferably about 35 cm.

On the other hand, the outer tube 2 is about 10 cm shorter than the inner tube 3 and is of a material which is stiffer as compared to the material of the inner tube 3.

FIGS. 2–6 show another embodiment of the instrument 16 according to the present invention.

Figure 2:
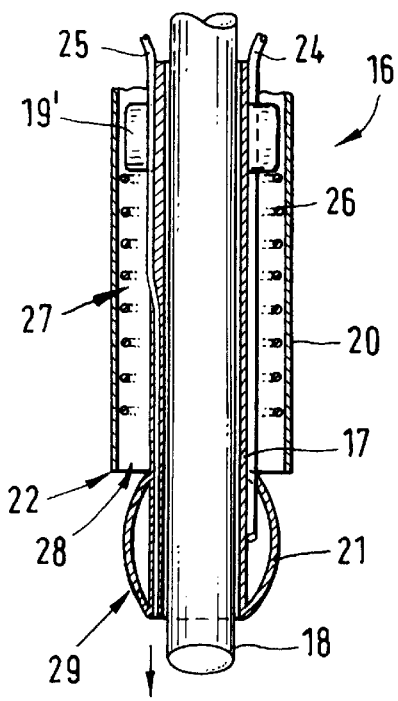
FIG. 2 is a schematic illustration of the distal end of a further embodiment of an instrument according to the present invention, shown with a stent inserted in the instrument.
Figure 3:
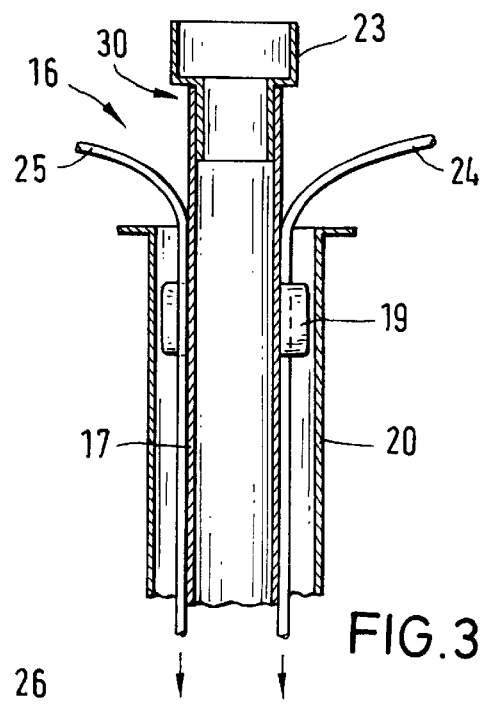
FIG. 3 is a schematic view of the proximal end of the instrument.

FIG. 2 shows a portion of the distal end, while FIG. 3 illustrates a portion of the proximal end of the instrument 16.

In inner tube 17 is guided over a fiber bronchoscope 18. Spacer members 19 serve to position and guide the inner tube 17 relative to the outer tube 20 and vice versa.

The inner tube 17 is equipped at its distal end 29 with a multi-purpose balloon 21. When the instrument 16 is inserted, the multi-purpose balloon may be expanded slightly in order to cover the end edges 22 of the outer tube 20. Damage to the vocal cords can be avoided in this manner.

As shown in FIG. 3, the inner tube 17 has at its proximal end 30 a standard tube adaptor 23. Also shown is a line 24 leading to the multi-purpose balloon 21 as well as an oxygen supply line 25.

For implanting a temperature-dependent stent 26 in the trachea, the stent 26 is placed in the space between the inner tube 17 and the outer tube 20, as shown in FIG. 2.

As seen from the distal end 29, the stent 26 is then located in the portion 27 between the balloon 21 and the first guide elements 19'. Sufficient space for a spontaneous respiration of the patient is available in the annular space 28 between the inner tube 17 and the outer tube 20.

After the stent 26 has been placed in the instrument 16, the instrument 16 is inserted.

Figure 5:
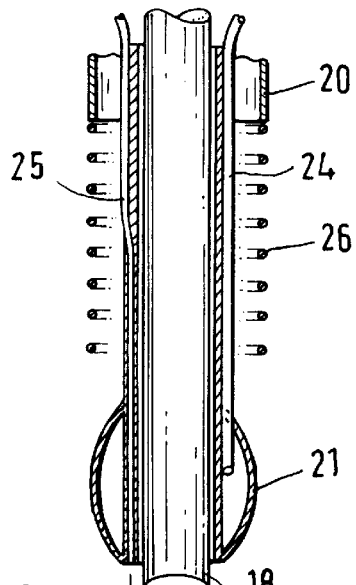
FIG. 5 is a schematic view of a first separation procedure during placement of a stent.
Figure 6:
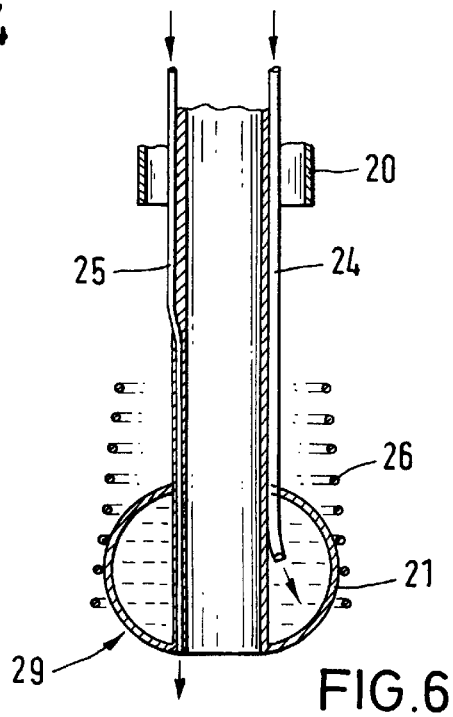
FIG. 6 is a schematic view showing the expansion of the stent by means of the cuff.

During the intubation, a visual control is effected by means of the fiber bronchoscope 18. Laser operations, dilation, etc., can also be carried out. After the stenosis has been passed, the outer shorter tube 20 is retracted, so that the self-expanding stent 26 is released. This situation is shown in FIG. 5. A correction of the position of the stent can be carried out by means of the balloon 28. After the stent 26 has reached its final position, the balloon 21 is filled with warm water, so that a complete expansion of the temperature-dependent stent is achieved. This process is schematically illustrated in FIG. 6.

Figure 7:
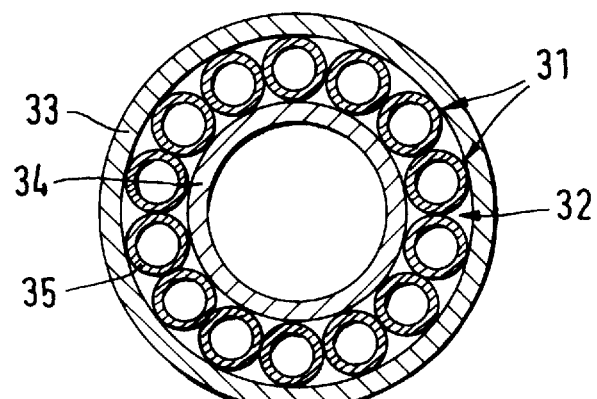
FIG. 7 is a cross-sectional view of another embodiment of an instrument according to the present instrument.

FIG. 7 is a cross-sectional view of an embodiment of the instrument according to the present invention with guide elements 31 which are components of a middle tube 32 with several ducts. The tube 32 is placed between the outer tube 33 and the inner tube 34. When a bronchoscope is inserted into the inner tube 34, a patient can safely breathe through the tube 32 formed by individual hose lines 35. Since the tubes 32, 33, 34 are displaceable relative to each other, the middle tube 32 can be adjusted in such a way that, adapted for the specific purpose, it forms an abutment for a stent to be placed.

Figure 8:
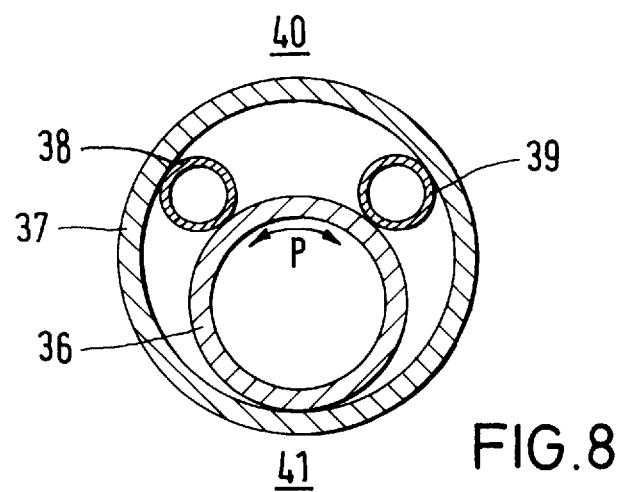
FIG. 8 is a cross-sectional view of another embodiment.

FIG. 8 shows an embodiment with an inner tube 36 mounted displaceably relative to the outer tube 37 and two guide elements 38, 39 between the inner tube 36 and the outer tube 37. By providing the two guide elements 38, 39, the inner tube 36 is guided eccentrically. This embodiment is advantageous for those cases in which it is the goal to have a greater distance on the side of the outer tube 37 denoted with 40 than on the side 41; this may be desirable, for example, in brachytherapy.

Of course, it is also possible to rotate the inner tube 36 within the outer tube 37, as indicated by double arrow P.

While specific embodiments of the invention have been shown and described in detail to illustrate the inventive principles, it will be understood that the invention may be embodied otherwise without departing from such principles.

I claim:

1. An instrument for flexible tracheoscopy/bronchoscopy, the instrument comprising an outer tube, an inner tube mounted within the outer tube so as to be axially displaceable relative to the outer tube, and at least one guide element for radially positioning the inner tube in the outer tube, the inner tube having a distal end, further comprising a cuff fillable with a medium at the distal end of the inner tube, wherein the at least one guide element is mounted within the space between the outer tube and the inner tube such that an axial position of the inner tube relative to the outer tube is adjustable at the distal end.

2. The instrument according to claim 1, wherein the at least one guide element is mounted on the inner tube.

3. The instrument according to claim 1, wherein a plurality of guide elements are supply lines mounted on the circumference of the inner tube.

4. The instrument according to claim 1, comprising a middle tube between the inner tube and the outer tube, the middle tube containing the at least one guide element.

5. The instrument according to claim 1, wherein the inner tube is configured to receive a bronchoscope or tracheoscopy.

6. The instrument according to claim 1, wherein the inner tube is of an opalescent material.

7. The instrument according to claim 6, wherein the inner tube is of a transparent but not opaque polyurethane.

8. The instrument according to claim 1, wherein the distal end of the inner tube is rounded.

* * * * *